(12) United States Patent
Akahane et al.

(10) Patent No.: US 9,433,338 B2
(45) Date of Patent: Sep. 6, 2016

(54) IMAGING ELEMENT, IMAGING DEVICE, ENDOSCOPE, ENDOSCOPE SYSTEM, AND METHOD OF DRIVING IMAGING ELEMENT

(71) Applicant: OLYMPUS CORPORATION, Tokyo (JP)

(72) Inventors: Nana Akahane, Hachioji (JP); Makoto Ono, Sagamihara (JP); Takahiro Nishiwaki, Tsukuba (JP); Katsumi Hosogai, Tsukuba (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/872,574

(22) Filed: Oct. 1, 2015

(65) Prior Publication Data

US 2016/0022117 A1    Jan. 28, 2016

Related U.S. Application Data

(63) Continuation of application No. PCT/JP2014/059455, filed on Mar. 31, 2014.

(30) Foreign Application Priority Data

Apr. 25, 2013  (JP) .................. 2013-092394

(51) Int. Cl.
*H04N 7/18* (2006.01)
*A61B 1/00* (2006.01)
(Continued)

(52) U.S. Cl.
CPC ....... *A61B 1/00006* (2013.01); *A61B 1/00009* (2013.01); *A61B 1/045* (2013.01);
(Continued)

(58) Field of Classification Search
CPC .... H04N 5/3698; H04N 5/361; H04N 5/357; H04N 5/363; H04N 5/378; H04N 5/2253; G02B 23/2476; A61B 1/045; A61B 1/05; A61B 1/00006; A61B 1/00009
See application file for complete search history.

(56) References Cited

U.S. PATENT DOCUMENTS 8,149,304 B2    4/2012  Murakami
2006/0114342 A1*  6/2006  Egawa .................. H04N 5/361
                                    348/241

(Continued)

FOREIGN PATENT DOCUMENTS

JP    H06-189200 A    7/1994
JP    H09-082931 A    3/1997
(Continued)

OTHER PUBLICATIONS

International Search Report dated Jul. 1, 2014 issued in PCT/JP2014/059455.
(Continued)

*Primary Examiner* — Jay Patel
*Assistant Examiner* — Neil Mikeska
(74) *Attorney, Agent, or Firm* — Scully, Scott, Murphy & Presser, PC (57) ABSTRACT

An imaging element includes: a plurality of pixels; first vertical transfer lines; a second vertical transfer line; a reference voltage generator configured to generate a first reference voltage for a column-black reference signal, a second reference voltage for a line-black reference signal and a third reference voltage for phase adjustment; a phase adjusting signal generator configured to output a phase adjusting signal corresponding to the third reference voltage; a first reference signal generator configured to generate a column-black reference signal corresponding to the first reference voltage; a second reference signal generator configured to generate a line-black reference signal corresponding to the second reference voltage; and a timing generator configured to drive the phase adjusting signal generator, the first reference signal generator and the second reference signal generator to transmit the phase adjusting signal, the column-black reference signal and the line-black reference signal, respectively.

6 Claims, 7 Drawing Sheets

(51) Int. Cl.
  *H04N 5/372*    (2011.01)
  *G02B 23/24*    (2006.01)
  *H04N 5/361*    (2011.01)
  *H04N 5/378*    (2011.01)
  *A61B 1/045*    (2006.01)
  *A61B 1/05*     (2006.01)
  *H04N 5/225*    (2006.01)

(52) U.S. Cl.
  CPC ............ *A61B 1/05* (2013.01); *G02B 23/2476* (2013.01); *H04N 5/2253* (2013.01); *H04N 5/361* (2013.01); *H04N 5/372* (2013.01); *H04N 5/378* (2013.01); *H04N 7/183* (2013.01); *H04N 2005/2255* (2013.01)

(56) References Cited

U.S. PATENT DOCUMENTS

| | | | | |
|---|---|---|---|---|
| 2008/0100736 | A1* | 5/2008 | Ise | H04N 5/232 348/311 |
| 2008/0291290 | A1* | 11/2008 | Sonoda | H04N 5/361 348/222.1 |
| 2010/0302415 | A1* | 12/2010 | Egawa | H04N 5/361 348/243 |
| 2011/0267513 | A1* | 11/2011 | Sonoda | H04N 5/361 348/294 |
| 2013/0021497 | A1* | 1/2013 | Kawamura | H04N 5/361 348/231.3 |

FOREIGN PATENT DOCUMENTS

| | | |
|---|---|---|
| JP | 2005-223860 A | 8/2005 |
| JP | 2007-194963 A | 8/2007 |
| JP | 2008-117304 A | 5/2008 |
| JP | 2010-093698 A | 4/2010 |
| JP | 2010-167201 A | 8/2010 |
| JP | 2011-109584 A | 6/2011 |
| JP | 2012-235193 A | 11/2012 |

OTHER PUBLICATIONS

Japanese Office Action dated Mar. 31, 2015 issued in JP 2015-509225.

Japanese Office Action dated Jul. 14, 2015 issued in JP 2015-509225.

* cited by examiner

BLACK REFERENCE SIGNAL PERIOD

PHASE SIGNAL PERIOD

IMAGING SIGNAL PERIOD

BLANKING PERIOD

IMAGING ELEMENT, IMAGING DEVICE, ENDOSCOPE, ENDOSCOPE SYSTEM, AND METHOD OF DRIVING IMAGING ELEMENT

CROSS-REFERENCE TO RELATED APPLICATIONS

This application is a continuation of PCT international application Ser. No. PCT/JP2014/059455 filed on Mar. 31, 2014 which designates the United States, incorporated herein by reference, and which claims the benefit of priority from Japanese Patent Applications No. 2013-092394, filed on Apr. 25, 2013, incorporated herein by reference.

BACKGROUND OF THE INVENTION

1. Field of the Invention

The present invention relates to an imaging element, an imaging device, an endoscope, an endoscope system, and a method of driving an imaging element.

2. Description of the Related Art

In an imaging device including a complementary metal-oxide semiconductor (CMOS) imaging element, power consumption differs between a blanking period and an imaging signal period. Thus in the initial part of the imaging signal period, fluctuation in power consumption causes the power source voltage to fluctuate, which results in distortion of an image.

To suppress such fluctuation in power consumption, provision of a circuit for supplying a current during a period where power consumption is low is proposed (for example, see Japanese Laid-open Patent Publication No. 2008-117304). In the technique disclosed in Japanese Laid-open Patent Publication No. 2008-117304, during a blanking period where the load current in a horizontal transfer circuit decreased to a predetermined threshold value or lower, a load circuit that operates by the same power source for the horizontal transfer circuit supplies a load current that compensates for a decreased amount of load current.

In the technique disclosed in Japanese Laid-open Patent Publication No. 2008-117304, a load circuit is provided to supply a current during a period where power consumption in an imaging element is low, so that a large amount of heat is generated in a chip, degrading the quality of an image under dark circumstances. Thus a conventional technique of providing a load circuit is inappropriate for an application in an endoscope, which is difficult to dissipate heat.

The present invention is made in view of the aforementioned problem. The object of the present invention is to provide an imaging element, an imaging device, an endoscope, and endoscope system, and a method of driving an imaging element that stabilizes a power source voltage and can suppress degradation in image quality.

SUMMARY OF THE INVENTION

An imaging element according to one aspect of the present invention includes: a plurality of pixels disposed in an arrangement of a two-dimensional matrix, the pixels being configured to receive external light to generate an imaging signal corresponding to a light amount and output the imaging signal; first vertical transfer lines, each first vertical transfer line being provided to each column in the arrangement of the plurality of pixels and transferring the imaging signal; a second vertical transfer line provided discretely from the first vertical transfer line; a reference voltage generator configured to generate a first reference voltage for a column-black reference signal, a second reference voltage for a line-black reference signal and a third reference voltage for phase adjustment; a phase adjusting signal generator configured to output a phase adjusting signal corresponding to the third reference voltage during a period in which the pixel does not output the imaging signal, the phase adjusting signal being used for the phase adjustment; a first reference signal generator including a first source follower transistor connected to the first vertical transfer line and a first reset transistor supplying an output voltage of the reference voltage generator to a gate of the first source follower transistor, and the first reference signal generator being configured to generate a column-black reference signal corresponding to the first reference voltage and output the column-black reference signal to the first vertical transfer line; a second reference signal generator including a second source follower transistor connected to the second vertical transfer line and a second reset transistor supplying the second reference voltage to a gate of the second source follower transistor, and the second reference signal generator being configured to generate a line-black reference signal corresponding to the second reference voltage and output the line-black reference signal to the second vertical transfer line; and a timing generator configured to drive the phase adjusting signal generator, the first reference signal generator and the second reference signal generator to transmit the phase adjusting signal, the column-black reference signal and the line-black reference signal, respectively to an external device during a transfer blanking period of the imaging signal.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

An endoscope system including an imaging device will be described below as an embodiment of the present invention (hereinafter referred to as "embodiment"). The embodiment does not limit the scope of the present invention. The same reference sign is appended to the same component in the drawings. It should be noted that the drawings are merely for schematic illustration, and the relation between thicknesses and widths of members, ratios among components, or the like are different from those of actual components. In addition, dimensions and ratios different among drawings are included.

EMBODIMENT

Figure 1:
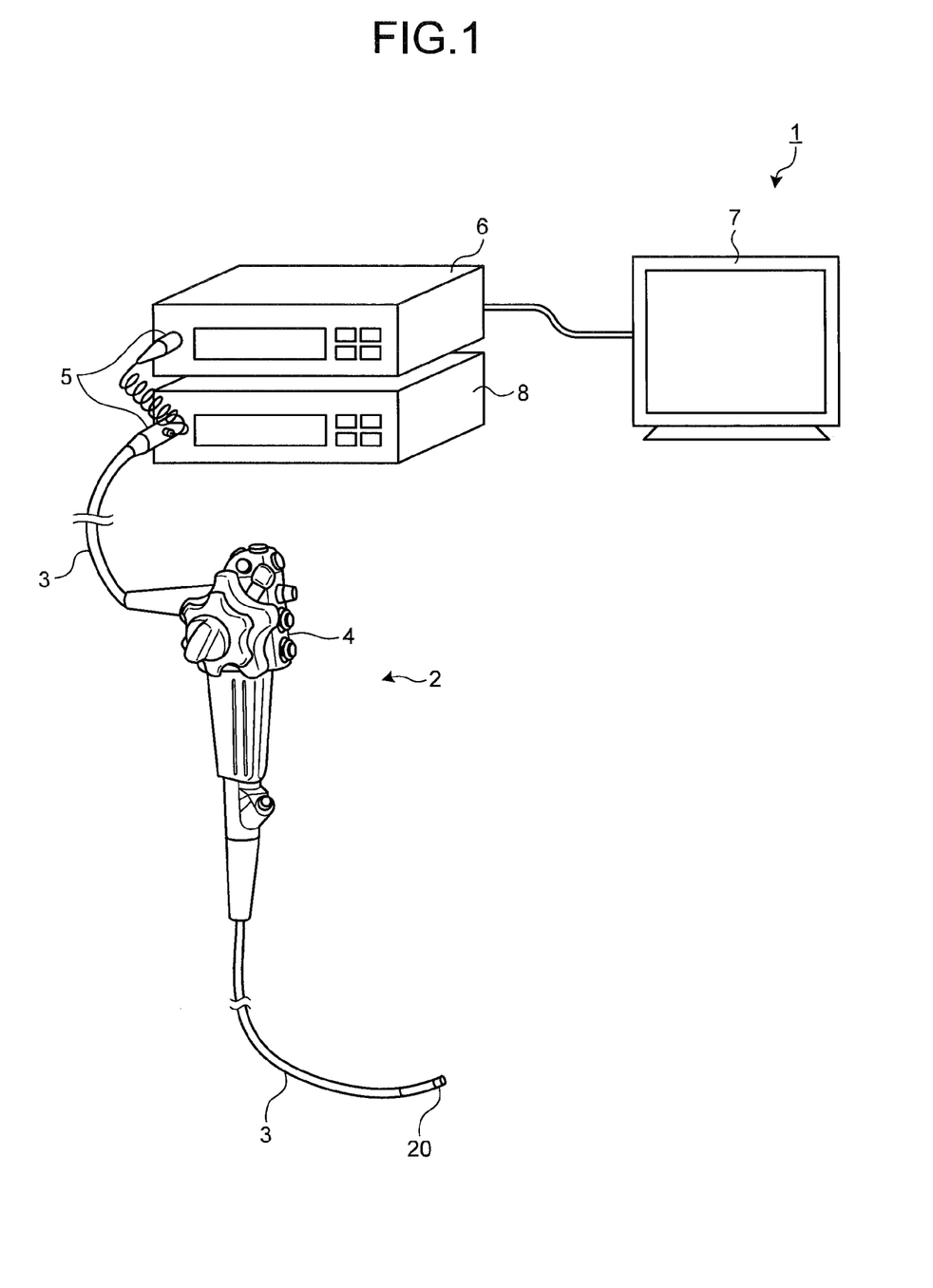
FIG. 1 schematically illustrates an overall configuration of an endoscope system according to an embodiment of the present invention.

FIG. 1 schematically illustrates an overall configuration of an endoscope system according to a first embodiment of the present invention. An endoscope system 1 illustrated in FIG. 1 includes an endoscope 2, a transmission cable 3, a connecting unit 5, a processor (control device) 6, a display device 7, and a light source device 8. The endoscope 2 is configured to take an in-vivo image in a subject with an insertion part which is a portion of the transmission cable 3 inserted in a body cavity of the subject and output imaging signals. The transmission cable 3 couples together the endoscope 2 and the connecting unit 5. The connecting unit 5 is coupled to the endoscope 2, the processor 6, and the light source device 8. The connecting unit 5 performs predetermined signal processing to imaging signals output from the coupled endoscope 2 and analogue-digital conversion (A/D conversion) to convert the imaging signals into image signals, and outputs image signals. The processor 6 performs predetermined image processing to image signals output from the connecting unit 5 and totally controls the endoscope system 1. The display device 7 displays image signals processed in the processor 6. The light source device 8 is configured with, for example, a white LED. Pulsed white light emitted from the light source device 8 passes through the connecting unit 5 and the transmission cable 3 and is emitted from the distal end of the insertion part of the endoscope 2 toward an object as illuminating light.

In the endoscope 2, an imaging unit (imaging device) 20 for taking in-vivo images is provided on the distal end side of the insertion part, at one end side of the transmission cable 3, to be inserted in a body cavity of the subject, and an operating unit 4 for receiving a command to be given to the endoscope 2 is connected to the proximal end side of the insertion part. The imaging unit 20 is coupled to the connecting unit 5 via the transmission cable 3 and the operating unit 4. Imaging signals of an image taken by the imaging unit 20 are output to the connecting unit 5 via the transmission cable 3 having a length of, for example, several meters.

Figure 2:
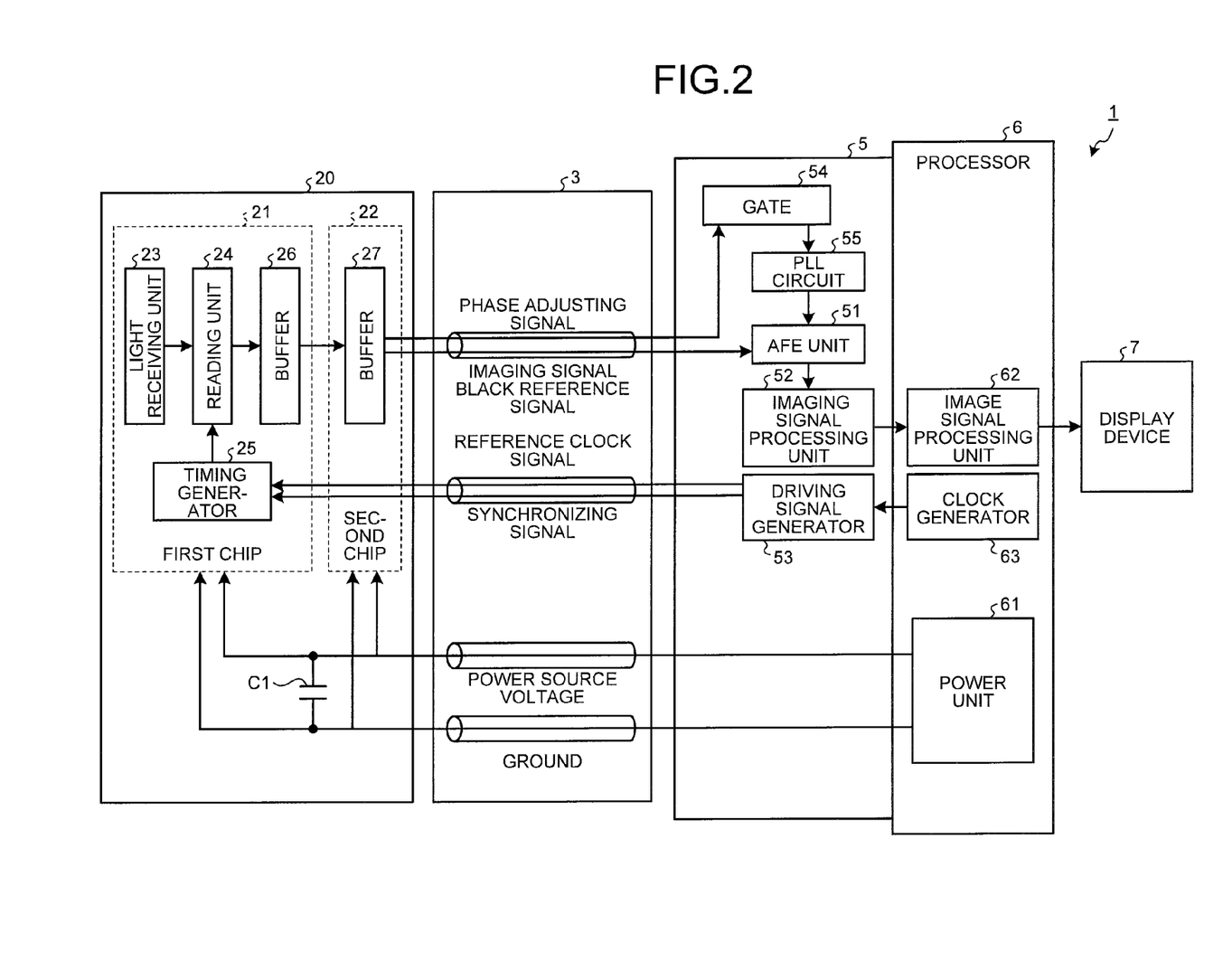
FIG. 2 is a block diagram illustrating a function of an essential portion of the endoscope system according to the embodiment of the present invention.

FIG. 2 is a block diagram illustrating a function of an essential portion of the endoscope system according to the first embodiment of the present invention. Details on components of the endoscope system 1 and a passage for electric signals in the endoscope system 1 will now be described referring to FIG. 2.

The imaging unit 20 includes a first chip (imaging element) 21 having a light receiving unit 23 and a second chip 22 having a buffer 27. The first chip 21 and the second chip 22 are bonded together so as to face each other. The chips are connected via a pad disposed on the periphery of the chips or a via hole or the like provided between the chips. The first chip 21 and the second chip 22 are not necessarily disposed with main surfaces thereof being parallel to each other. The first chip 21 and the second chip 22 may be disposed side by side or disposed with a main surface being vertical to the other main surface, depending on the surrounding structure.

The first chip 21 of the imaging unit 20 includes the light receiving unit 23 on which a plurality of unit pixels is arrayed along the line-direction and the column-direction, that is in a two-dimensional matrix arrangement, a reading unit 24 for reading imaging signals resulting from photoelectric conversion performed in the light receiving unit 23, a timing generator 25 which generates a timing signal based on a reference clock signal and a synchronizing signal transmitted from the connecting unit 5 and supplies a timing signal to the reading unit 24, and a buffer (multiplexer) 26 which outputs an imaging signal to the second chip 22. Further details on the configuration of the first chip 21 will be described later referring to FIG. 3.

The second chip 22 of the imaging unit 20 includes a buffer 27 serving as a transmitter that transmits only alternate components in output imaging signals from the first chip 21 to the processor 6 via the transmission cable 3 and the connecting unit 5. The combination of circuits mounted on the first chip 21 and the second chip 22 may suitably be changed by design requirements.

The imaging unit 20 can receive a power source voltage (VDD) generated in a power unit 61 in the processor 6 and the ground (GND) via the transmission cable 3. A capacitor C1 for stabilizing the power source is provided between the power source voltage (VDD) and the ground (GND) supplied to the imaging unit 20.

The imaging unit 20 transmits a phase adjusting signal, a black reference signal, and an imaging signal to the connecting unit 5 via the transmission cable 3.

The connecting unit 5 includes an analogue front end (AFE) unit 51, an imaging signal processing unit 52, a driving signal generator 53, a gate 54, and a PLL circuit 55. The connecting unit 5 electrically couples the endoscope 2 (imaging unit 20) and the processor 6, and serves as a relay processor that relays electric signals. The connecting unit 5 and the imaging unit 20 are coupled via the transmission cable 3. The connecting unit 5 and the processor 6 are coupled via, for example, a coil cable. The connecting unit 5 is also coupled to the light source device 8.

After performing matching of impedance in a passive element, such as a resistance, to a received imaging signal transmitted from the imaging unit 20, the AFE unit 51 derives an AC component in a capacitor to determine an operating point by a partial resistance. Then the AFE unit 51 converts an analogue imaging signal into a digital imaging signal through analogue-digital (A/D) conversion and transmits the digital imaging signal to the imaging signal processing unit 52.

The imaging signal processing unit 52 is configured with, for example, a field programmable gate array (FPGA), and performs predetermined signal processing, such as removal of vertical lines, denoising, and removal of common mode noise, to a digital imaging signal which is input from the AFE unit 51.

The driving signal generator 53 generates a synchronizing signal representing the start point of each frame, based on a reference clock signal (e.g., a clock signal of 27 MHz) which is supplied from the processor 6 and used as a reference for operating components of the endoscope 2. The driving signal generator 53 outputs the generated synchronizing signal together with the reference clock signal to the timing generator 25 of the imaging unit 20 via the transmission cable 3, in other words, via the insertion part which is a portion of the transmission cable 3. The generated synchronizing signal includes a horizontal synchronizing signal and a vertical synchronizing signal.

The gate 54 is opened during a period when the imaging unit 20 transmits phase adjusting signals which are thus input to the PLL circuit 55. The PLL circuit 55 compares a phase adjusting signal and a sampling pulse for sampling imaging signals during the imaging signal period to control a sampling phase of an imaging signal in the AFE unit 51.

The processor 6 includes a power unit 61, an image signal processing unit 62, and a clock generator 63. The processor 6 is a control device for totally controlling the endoscope system 1. The power unit 61 generates a power source voltage (VDD) and supplies the generated power source voltage and the ground (GND) to the imaging unit 20 via the connecting unit 5 and the transmission cable 3. The image signal processing unit 62 performs a predetermined image processing and conversion to a processed, for example, denoised digital imaging signal in the imaging signal processing unit 52 to obtain an image signal, and outputs the image signal to the display device 7. The clock generator 63 outputs a reference clock signal to the driving signal generator 53.

The display device 7 displays an image taken by the imaging unit 20 based on image signals. The image processing performed in the image signal processing unit 62 is, for example, synchronizing processing, white balance (WB) adjusting processing, gain adjusting processing, gamma correcting processing, digital-analogue (D/A) conversion processing, and a format conversion processing.

Figure 3:
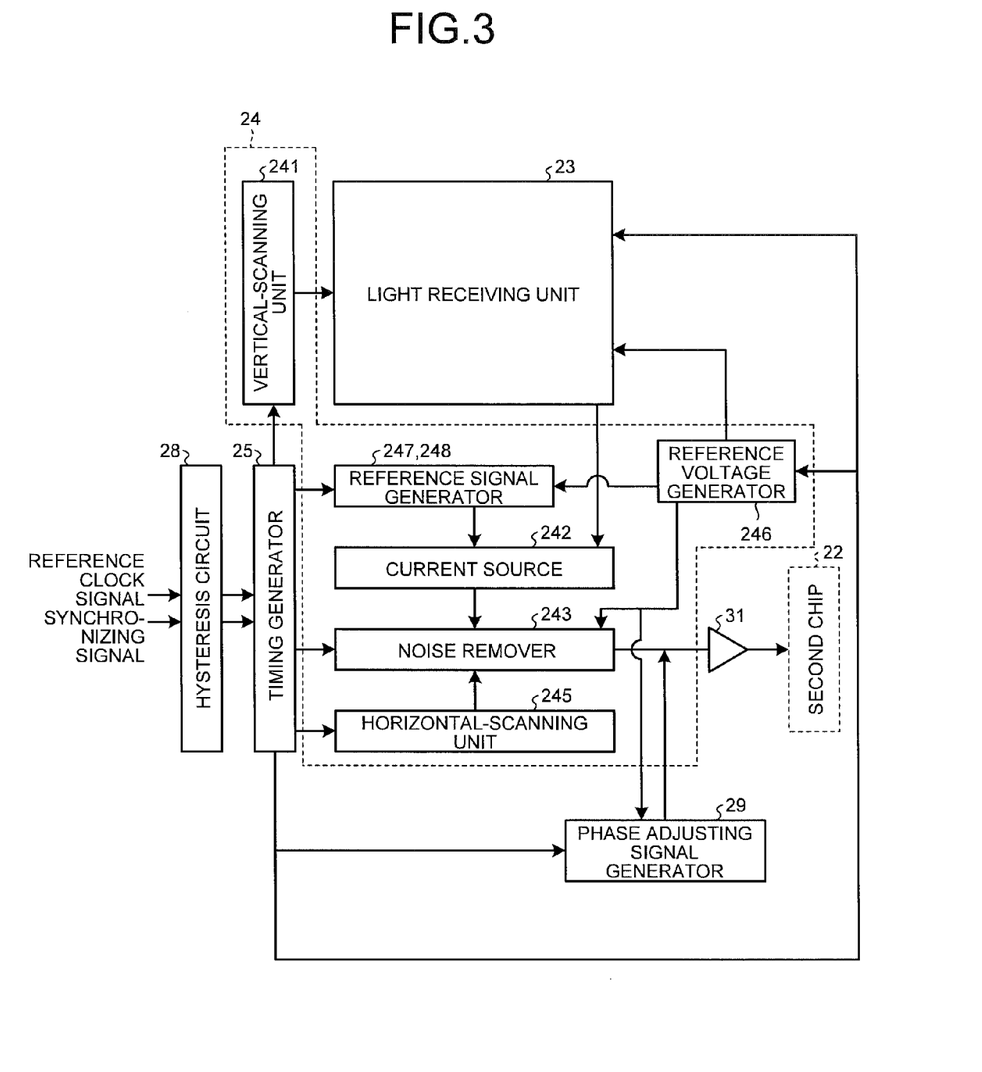
FIG. 3 is a block diagram illustrating a detailed configuration of a first chip illustrated in FIG. 2.
Figure 4:
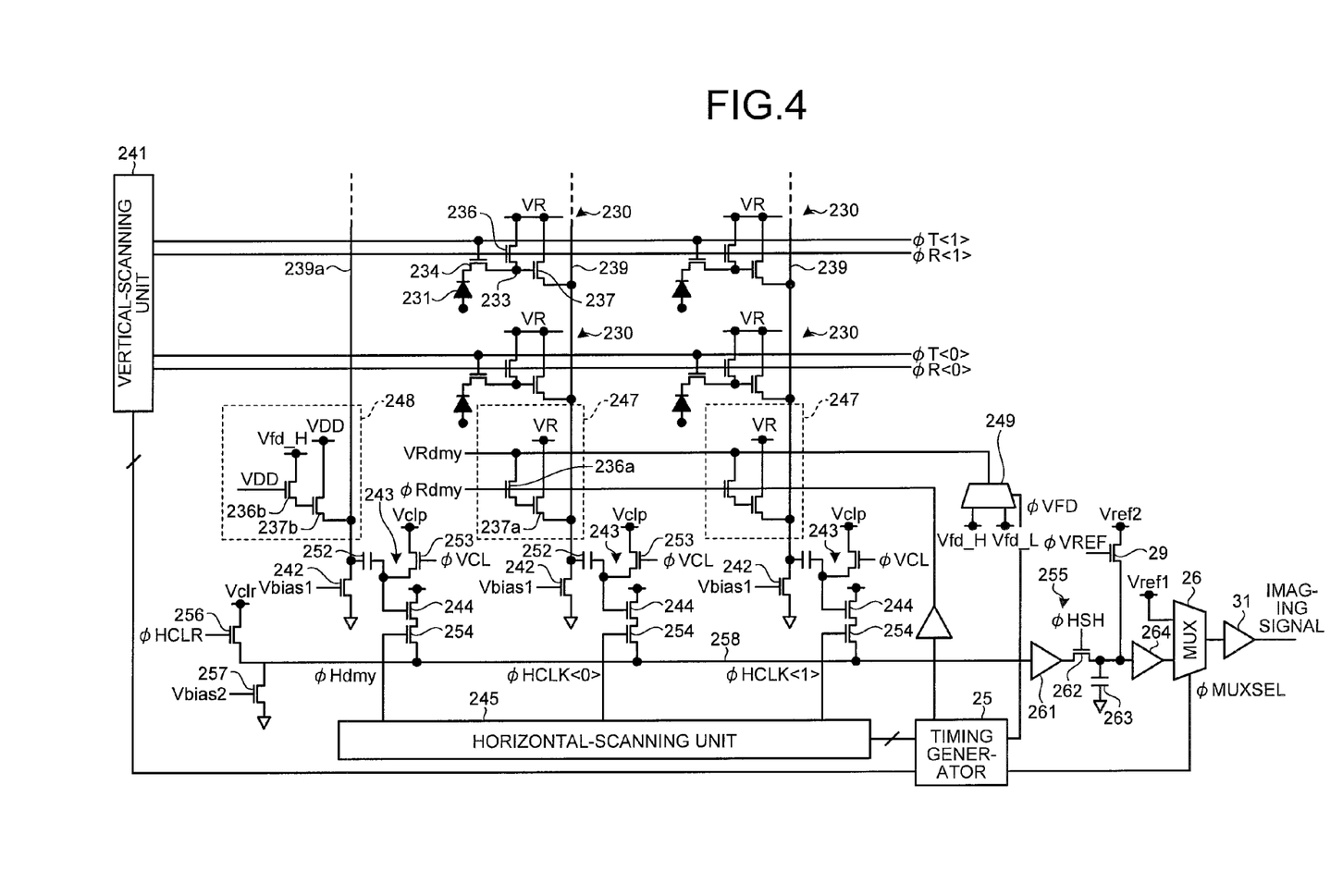
FIG. 4 is a circuit diagram illustrating a configuration of the first chip of the endoscope system according to the embodiment of the present invention.

FIG. 3 is a block diagram illustrating a detailed configuration of the first chip illustrated in FIG. 2. FIG. 4 is a circuit diagram illustrating a configuration of the first chip of the endoscope system according to the first embodiment. The first chip 21 has, for example, the light receiving unit 23, the reading unit (driving unit) 24, the timing generator 25, the multiplexer 26, a hysteresis circuit 28, and a phase adjusting signal generator 29 mounted thereon.

The reading unit 24 includes a vertical-scanning unit (line selector) 241, a current source 242, a noise remover 243, a horizontal-scanning unit (column selector) 245, a reference voltage generator 246, and reference signal generators 247 and 248.

The timing generator 25 generates various types of driving signal based on reference clock signals shaped in the hysteresis circuit 28 and synchronizing signals, and supplies generated drive signals to the phase adjusting signal generator 29, the vertical-scanning unit 241, the noise remover 243, the horizontal-scanning unit 245, the reference voltage generator 246, the reference signal generators 247 and 248, and the multiplexer 26 and a multiplexer 249.

The hysteresis circuit 28 shapes the waveforms of a reference clock signal and a synchronizing signal that are transmitted a long distance through the transmission cable 3. The reference clock signal and a synchronizing signal shaped in the hysteresis circuit 28 are input to the timing generator 25.

The phase adjusting signal generator 29 generates and outputs a phase adjusting signal used for phase adjustment in the connecting unit 5. The phase adjusting signal generator 29 will be described in detail later.

The vertical-scanning unit 241 impresses selected line <M> (M=0, 1, 2, ..., m−1, m) in the light receiving unit 23 with line selecting pulses φT<M> and φR<R> based on drive signals (e.g., φT, φR) supplied from the timing generator 25 to drive each unit pixel 230 of the light receiving unit 23 by the current source 242. An imaging signal and a noise signal during reset of a pixel is transferred by the vertical-scanning unit 241 to a vertical transfer line (first transfer line) 239 to be output to the noise remover 243.

The noise remover 243 eliminates variation in output among unit pixels 230 and noise signals during reset of a pixel, and then outputs an imaging signal resulting from photoelectric conversion performed in each unit pixel 230. The noise remover 243 will be described in detail later.

The horizontal-scanning unit 245 impresses a selected column <N> (N=0, 1, 2, ..., n−1, n) in the light receiving unit 23 with column selecting pulse φHCLK<N> based on a drive signal (φHCLK) supplied from the timing generator 25 to transfer an imaging signal resulting from photoelectric conversion performed in each unit pixel 230 to a horizontal transfer line (second transfer line) 258 via the noise remover 243 to be output to a sample and hold unit 255.

A large number of unit pixels (photoelectric converters) 230 is arranged in a two-dimensional matrix in the light receiving unit 23 of the first chip 21. Each unit pixel 230 includes a photoelectric conversion element (photodiode) 231, a charge converter 233, a transfer transistor (first transfer unit) 234, a pixel resetting unit (transistor) 236, and a pixel source follower transistor 237. In the description, one or more photoelectric conversion elements and a transfer transistor for transferring a signal charge from each photoelectric conversion element to the charge converter 233 are referred to as a unit cell. That is, a unit cell includes a set of one or more photoelectric conversion elements and a transfer transistor, and each unit pixel 230 includes one unit cell.

The photoelectric conversion element 231 converts incident light into a signal charge amount corresponding to the light amount through photoelectric conversion and accumulates the signal charge amount. The cathode side of the photoelectric conversion element 231 is connected to one end of the transfer transistor 234 and the anode side of the photoelectric conversion element 231 is connected to the ground GND. The charge converter 233 composed of a floating diffusion capacitor (FD) converts the charge accumulated in the photoelectric conversion element 231 into a voltage.

The transfer transistor 234 transfers a charge from the photoelectric conversion element 231 to the charge converter 233. The gate of the transfer transistor 234 is connected to a signal line to which driving pulse (line selecting pulse) φT is supplied, and the other end is connected to the charge converter 233. When the drive signal φT is supplied from the vertical-scanning unit 241 via the signal line, the transfer transistor 234 is set to the on-state allowing a signal charge to be transferred from the photoelectric conversion element 231 to the charge converter 233.

The pixel resetting unit (transistor) 236 resets the charge converter 233 to a predetermined potential. One end of the pixel resetting unit 236 is connected to variable voltage VR, and the other end is connected to the charge converter 233. The gate of the pixel resetting unit 236 is connected to a signal line to which drive signal φR is supplied. When the drive signal φR is supplied from the vertical-scanning unit 241 via the signal line, the pixel resetting unit 236 is set to the on-state and the signal charge accumulated in the charge converter 233 is discharged, thereby resetting the charge converter 233 to be at a predetermined potential.

One end of the pixel source follower transistor (pixel amplifier) 237 is connected to the variable voltage VR, and the other end is connected to the vertical transfer line 239. A signal resulting from voltage conversion performed in the charge converter 233 (an imaging signal or a signal during reset) is input to the gate. When the drive signal φT is supplied to the gate of the transfer transistor 234 after a selecting operation which will be described later, a charge is read out from the photoelectric conversion element 231, and the charge converter 233 performs voltage conversion to the charge. The converted charge is transferred to the vertical transfer line 239 via the pixel source follower transistor 237.

In the embodiment, by supplying the drive signal φR to the gate of the pixel resetting unit 236 when the variable voltage VR is at a level of the power source voltage VDD (e.g., 3.3 V), the pixel source follower transistor 237 is set to the on-state, and the unit pixel including the pixel resetting unit 236 is selected (selecting operation). By supplying the drive signal φR to the gate of the pixel resetting unit 236 when the variable voltage VR is at a level of deselecting voltage Vfd_L (e.g., 1 V), the pixel source follower transistor 237 is set to the off-state, and the unit pixel including the pixel resetting unit 236 is deselected (deselecting operation).

The reference signal generator 247 is provided to each column of the unit pixel 230 at the same pitch as unit pixels 230, and includes the reference signal generation reset unit (transistor) 236a and a reference signal generation source follower transistor 237a. That is, the reference signal generator 247 has a configuration same as the unit pixel 230 without the photoelectric conversion element (photodiode) 231, the charge converter 233, and the transfer transistor (first transfer unit) 234.

The reference signal generation reset unit 236a holds the gate of the reference signal generation source follower transistor 237a at a predetermined potential. One end of the reference signal generation reset unit 236a is connected to the multiplexer 249, and the other end is connected to the gate of the reference signal generation source follower transistor 237a. A signal line to which drive signal φRdmy is supplied is connected to the gate.

Instructed by a drive signal (φVFD) supplied from the timing generator 25, the multiplexer 249 alternately outputs reference signal voltage Vfd_H and the deselecting voltage Vfd_L supplied from the reference voltage generator 246 (a reference voltage generator 246a illustrated in FIG. 5A and a reference voltage generator 246b illustrated in FIG. 5B) as variable voltage VRdmy.

When the drive signal φRdmy is supplied from the timing generator 25 via the signal line to the gate of the reference signal generation reset unit 236a, the reference signal generation reset unit 236a is set to the on-state and the gate of the reference signal generation source follower transistor 237a is held at a predetermined potential (VRdmy: Vfd_H or Vfd_L).

One end of the reference signal generation source follower transistor 237a is connected to the variable voltage VR supplied from the reference voltage generator 246 (the reference voltage generator 246a illustrated in FIG. 5A), and the other end is connected to the vertical transfer line 239. The reference signal voltage Vfd_H or the deselecting voltage Vfd_L is input to the gate. When a selecting operation which will be described later is performed, a signal corresponding to the reference signal voltage Vfd_H (a first reference signal or a column-black reference signal) is transferred to the vertical transfer line 239 via the reference signal generation source follower transistor 237a.

In the embodiment, as in a similar manner as the normal unit pixel 230, by supplying the drive signal φRdmy to the gate of the reference signal generation reset unit 236a when the variable voltage VR is at a level of the power source voltage VDD (e.g., 3.3 V) and VRdmy is Vfd_H (e.g., 2 V), the reference signal generation source follower transistor 237a is set to the on-state, and the reference signal generator 247 including the reference signal generation reset unit 236a is selected (selecting operation). By supplying the drive signal φRdmy to the gate of the reference signal generation reset unit 236a when the variable voltage VR is at a level of the deselecting voltage Vfd_L (e.g., 1 V) and VRdmy is Vfd_L (e.g., 1 V), the reference signal generation source follower transistor 237a is set to the off-state, and the reference signal generator 247 including the reference signal generation reset unit 236a is deselected (deselecting operation).

The reference signal generator 248 is connected to a dedicated vertical transfer line 239a not to a column of the unit pixel 230. The reference signal generator 248 includes the reference signal generation reset unit (transistor) 236b and a reference signal generation source follower transistor 237b. That is, the reference signal generator 247 has a configuration same as the unit pixel 230 without the photoelectric conversion element (photodiode) 231, the charge converter 233, and the transfer transistor (first transfer unit) 234.

The reference signal generation reset unit 236b holds the gate of the reference signal generation source follower transistor 237b at a predetermined potential. One end of the reference signal generation reset unit 236b is connected to the reference signal voltage Vfd_H supplied from the reference voltage generator 246b illustrated in FIG. 5B, and the other end is connected to the gate of the reference signal generation source follower transistor 237b. A signal line to which the power source voltage VDD is supplied is connected to the gate of the reference signal generation reset unit 236b. Since the gate of the reference signal generation reset unit 236b is connected to the signal line to which the power source voltage VDD is supplied, the reference signal generation reset unit 236b always holds the gate of the reference signal generation source follower transistor 237b at a potential of Vfd_H.

One end of the reference signal generation source follower transistor 237b is connected to VDD, and the other end is connected to the vertical transfer line 239a. The reference signal voltage Vfd_H is input to the gate. A signal corresponding to the reference signal voltage Vfd_H (a second reference signal or a line-black reference signal) is transferred to the vertical transfer line 239a via the reference signal generation source follower transistor 237b.

The vertical transfer line 239a dedicated to the reference signal generator 248 is configured in a manner similar to the normal vertical transfer line 239 except that connection is made to the reference signal generator 248 instead to a plurality of lines of unit pixels 230. Similarly to an imaging signal transferred through the vertical transfer line 239, a black reference signal transferred through the vertical transfer line 239a is input to the noise remover 243.

One end of the current source 242 is connected to the vertical transfer line 239, and the other end is connected to the ground GND. The gate is impressed with bias voltage Vbias1. The unit pixel 230 and the reference signal generator 247 are driven by the current source 242 to read out an output (imaging signal) from the unit pixel 230 and an output (black reference signal) from the reference signal generator 247 into the vertical transfer line 239. Signals (an imaging signal and a black reference signal) read out into the vertical transfer line 239 are input to the noise remover 243.

The noise remover 243 includes a transfer capacitor (AC coupling capacitor) 252 and a clamp switch (transistor) 253. One end of the transfer capacitor 252 is connected to the vertical transfer line 239, and the other end is connected to a column source follower transistor 244. One end of the clamp switch 253 is connected to a signal line to which clamp voltage Vclp is supplied from the reference voltage generator 246 (the reference voltage generator 246b illustrated in FIG. 5B). The other end of the clamp switch 253 is connected between the transfer capacitor 252 and the column source follower transistor 244. Drive signal φVCL is input to the gate from the timing generator 25. An imaging signal input to the noise remover 243 includes a noise component.

When the drive signal φVCL from the timing generator 25 is input to the gate of the clamp switch 253, the clamp switch 253 is set to the on-state, and the transfer capacitor 252 is reset by the clamp voltage Vclp supplied from the reference voltage generator 246. A black reference signal and an imaging signal from which noise is removed in the noise remover 243 are input to the gate of the column source follower transistor 244.

Since the noise remover 243 does not require a capacitor for sampling (sampling capacitor), the transfer capacitor (AC coupling capacitor) 252 is only required to have a large enough capacity compared to the input capacity of the column source follower transistor 244. In addition, without a sampling capacitor, the area occupied by the noise remover 243 in the first chip 21 can be reduced.

One end of the column source follower transistor 244 is connected to the power source voltage (VDD), and the other end is connected to one end of a column selecting switch (second transfer unit) 254. An imaging signal and a black reference signal are input to the gate via the noise remover 243. On end of the column selecting switch 254 is connected to the other end of the column source follower transistor 244, and the other end of the column selecting switch 254 is connected to the horizontal transfer line (second transfer line) 258.

One end of a horizontal reset transistor 256 is connected to the horizontal reset voltage Vclr, and the other end is connected to the horizontal transfer line 258. Drive signal φHCLR from the timing generator 25 is input to the gate of the horizontal reset transistor 256. When the drive signal φHCLR from the timing generator 25 is input to the gate of the horizontal reset transistor 256, the horizontal reset transistor 256 is set to the on-state, and the horizontal transfer line 258 is reset.

On end of the column selecting switch 254 is connected to the other end of the column source follower transistor 244, and the other end is connected to the horizontal transfer line (second transfer line) 258. A signal line for supplying drive signal φHCLK<N> from the horizontal-scanning unit 245 is connected to the gate of the column selecting switch 254. When the drive signal φHCLK<N> from the horizontal-scanning unit 245 is supplied to the gate of the column selecting switch 254 on column <N>, the column selecting switch 254 is set to the on-state, and signals (an imaging signal and a black reference signal) in the vertical transfer line 239 on column <N> are transferred to the horizontal transfer line 258.

One end of a constant current source 257 is connected to the horizontal transfer line 258, and the other end is connected to the ground GND. The gate is impressed with bias voltage Vbias2. The constant current source 257 drives the column source follower transistor 244 to read out an imaging signal and a black reference signal from the vertical transfer line 239 into the horizontal transfer line 258.

Signals read out into the horizontal transfer line 258 is input to the sample and hold unit 255. The sample and hold unit 255 includes a buffer 261, a sample and hold switch (transistor) 262, a sample capacitor (capacitor) 263, and an operational amplifier 264. The horizontal transfer line 258 is connected to the input of the buffer 261. A black reference signal, an imaging signal, and a horizontal reset voltage (Vclr) are input to the buffer 261 via the horizontal transfer line 258. The output of the buffer 261 is connected to one end of the sample and hold switch 262. The other end of the sample and hold switch 262 is connected to the input of the operational amplifier 264. One end of the sample capacitor 263 is connected to the other end of the sample and hold switch 262 and to the input of the operational amplifier 264. The other end of the sample capacitor 263 is connected to the ground GND. The output of the operational amplifier 264 is connected to an inverting input terminal of the operational amplifier 264 and to the input of the multiplexer 26. The sample and hold unit 255 holds the sample capacitor 263 at a voltage immediately before the sample and hold switch 262 is set to the off-state so that the voltage kept in the sample capacitor 263 is output while the sample and hold switch 262 is in the off-state.

In the embodiment, cross talk of imaging signals across columns can be suppressed by alternately performing readout of a noise-removed imaging signal from the vertical transfer line 239 and reset of the horizontal transfer line 258 by the horizontal reset transistor 256. In addition, by setting the sample and hold switch 262 of the sample and hold unit 255 to the on-state when transferring a noise-removed imaging signal and to the off-state when transferring a noise signal during reset, only noise-removed imaging signals can be output to the operational amplifier 264. Since the first chip 21 includes the sample and hold unit 255, the band of the amplifier circuit in the downstream can be reduced by half and a range can be suppressed.

The phase adjusting signal generator 29 is a switch composed of a MOS transistor. One end of the phase adjusting signal generator 29 is connected to a signal line for supplying reference voltage Vref2 generated in a reference voltage generator 246c (see FIG. 5C), and the other end of the phase adjusting signal generator 29 is connected between the connection node connecting the other end of the sample and hold switch 262 and the sample capacitor 263 and the input of the operational amplifier 264. The gate is connected to a signal line to which drive signal φVREF is supplied. When the drive signal φVREF is in the high-state, the phase adjusting signal generator 29 outputs the reference voltage Vref2 generated in the reference voltage generator 246c (see FIG. 5O). During a period when the phase adjusting signal generator 29 is outputting phase adjusting signals, the sample and hold switch 262 is kept in the off-state, so that only phase adjusting signals are input to the multiplexer 26 in the downstream.

The multiplexer 26 is driven by a drive signal (φMUXSEL) supplied from the timing generator 25 to alternately output signals input from the sample and hold unit 255 (a black reference signal, an imaging signal, and a phase adjusting signal) and the reference voltage Vref1 generated in the reference voltage generator 246b (see FIG. 5B) to an output unit 31. The output unit 31 performs signal amplification of a noise-removed imaging signal and the reference voltage Vref1 as required and alternately outputs resulting signals and voltage to the second chip 22. The output reference voltage Vref1 is used in, for example, the imaging signal processing unit 52 of the connecting unit 5 to remove common mode noise superimposed during transmission of imaging signals in the transmission cable 3.

In the second chip 22, black reference signals (first and second reference signals), imaging signals, and phase adjusting signals are transmitted to the connecting unit 5 via the transmission cable 3.

Figure 5A:
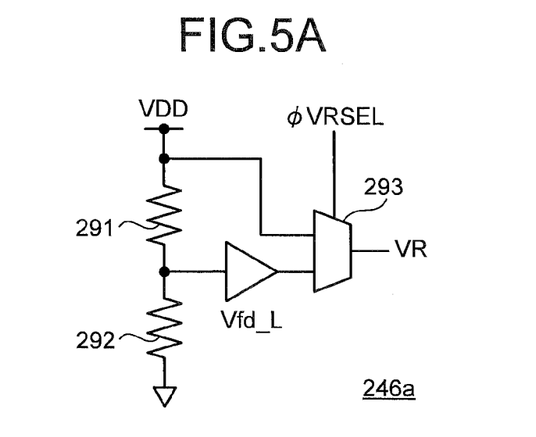
FIG. 5A is a circuit diagram illustrating a configuration of a reference voltage generator of a light receiving unit of the endoscope system according to the embodiment of the present invention.
Figure 5B:
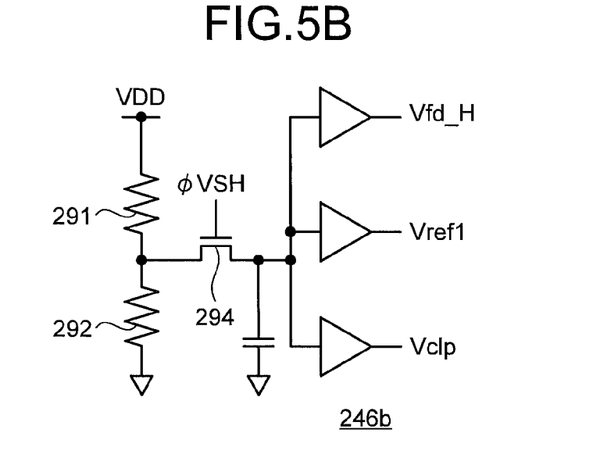
FIG. 5B is a circuit diagram illustrating a configuration of a reference voltage generator of the light receiving unit of the endoscope system according to the embodiment of the present invention.
Figure 5C:
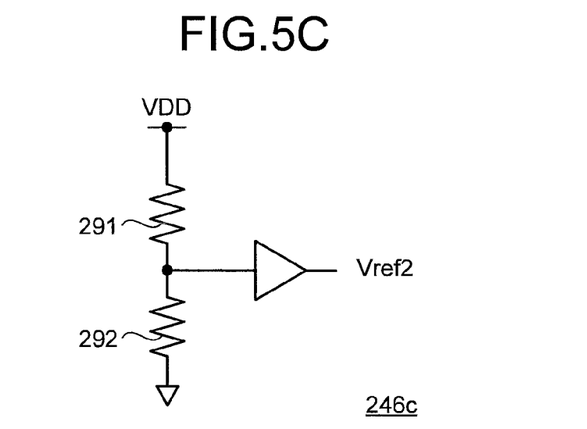
FIG. 5C is a circuit diagram illustrating a configuration of a reference voltage generator of the light receiving unit of the endoscope system according to the embodiment of the present invention.

FIGS. 5A to 5C are circuit diagrams illustrating configurations of the reference voltage generators of the light receiving unit of the endoscope system according to the embodiment.

The reference voltage generator 246a illustrated in FIG. 5A includes a resistance voltage dividing circuit composed of two resistances 291 and 292 and a multiplexer 293 driven by drive signal φVRSEL.

Instructed by the drive signal φVRSEL input from the timing generator 25, the multiplexer 293 impresses the whole pixels and the reference signal generator 247 with the variable voltage VR that are alternately selected from the power source voltage VDD (e.g., 3.3 V) and the deselecting voltage Vfd_L (e.g., 1 V) generated in the resistance voltage dividing circuit.

The reference voltage generator 246b illustrated in FIG. 5B includes a resistance voltage dividing circuit composed of two resistances 291 and 292 and a switch (transistor) 294 driven by drive signal φVSH. Driven at a timing when the switch 294 activates the driving signal φVSH, the reference voltage generator 246b generates the reference signal voltage Vfd_H (e.g., 2 V), the clamp voltage Vclp for the noise remover 243, and the reference voltage Vref1 from the power source voltage VDD.

Since the reference voltage Vref1 and the clamp voltage Vclp are generated from the same power source at the same timing, the reference voltage Vref1 reflects the effect of fluctuation in the power source on imaging signals output from the noise remover 243. In addition, the reference voltage Vref1 reflects information on the transmission noise in the transmission cable 3 during transmission. Therefore, by alternately transmitting noise-removed imaging signals and the reference voltage Vref1 to the connecting unit 5, a process of removing noise, such as correlated double sampling, can be performed in the connecting unit 5 to obtain imaging signals in which the noise received during transmission is removed.

The reference voltage generator 246c illustrated in FIG. 5C includes a resistance voltage dividing circuit composed of two resistances 291 and 292. The reference voltage generator 246c generates the reference voltage Vref2 from the power source voltage VDD. The reference voltage Vref2 is output from the phase adjusting signal generator 29 as a phase adjusting signal.

Figure 6:
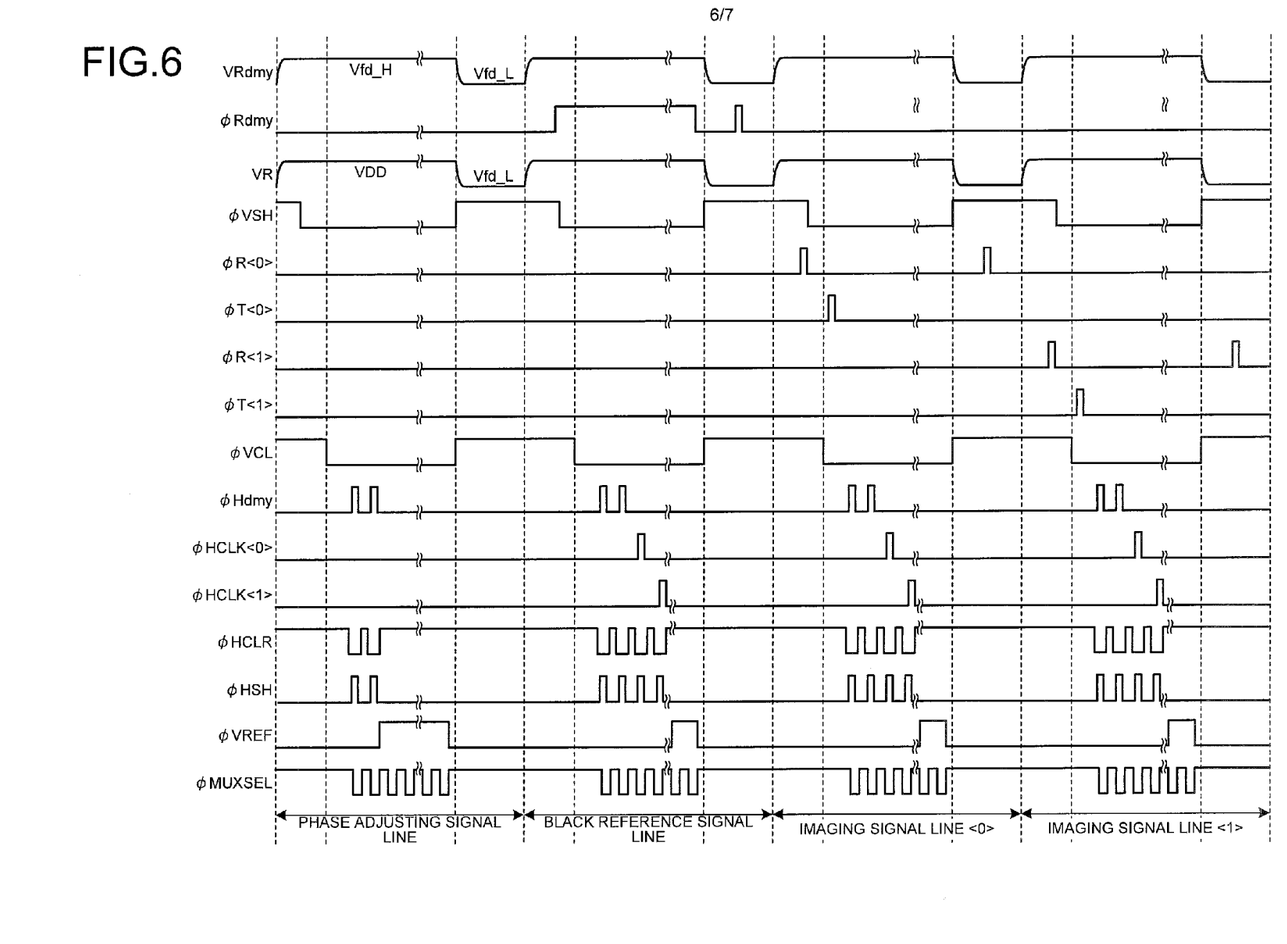
FIG. 6 is a timing diagram illustrating a drive timing of an imaging device according to the embodiment of the present invention.

FIG. 6 is a timing diagram illustrating a drive timing of an imaging device according to the embodiment of the present invention. Illustrated in the drawing are, from the topmost in sequence, variable voltage VRdmy (reference signal voltage Vfd_H and deselecting voltage Vfd_L), drive signal φRdmy, variable voltage VR, drive signal φVSH, drive signals φR, φT, φVCL, φHdmy, φHCLK, φHCLR, φHSH, φVREF, and φMUXSEL.

A phase adjusting signal line is first output. The variable voltage VRdmy is set to a level of the reference signal voltage Vfd_H (e.g., 2 V) and the variable voltage VR is set to a level of VDD (e.g., 3.3 V). In this state, by switching the clamp switch 253 from the on-state (φVCL: high) to the off-state (φVCL: low), the gate of the column source follower transistor 244 is set to the clamp voltage Vclp. The clamp voltage Vclp is determined by the timing of falling of the φVSH, and the reference signal voltage Vfd_H and the reference voltage Vref1 are also determined at this timing. Since φRdmy and φR are kept off (low), a line-black reference signal generated in the reference signal generator 248 which is always selected is output.

After sampling the line-black reference signal taking the clamp voltage Vclp as a reference, the horizontal reset transistor 256 is turned off (φHCLR: low) to cancel the reset-state of the horizontal transfer line 258, the column selecting switch 254 provided in the most-downstream of the vertical transfer line 239a is turned on (driving pulse φHdmy: high), and the sample and hold switch 262 is turned on (driving pulse φHSH: high) in a pulsed manner, and thereby the line-black reference signal is transferred to the horizontal transfer line 258 to be sampled by the sample capacitor 263. The multiplexer 26 is impressed with driving pulse φMUXSEL of low level to output the line-black reference signal sampled by the sample capacitor 263 to the output unit 31. In this state, synchronizing with a driving pulse for the multiplexer 26, the horizontal reset transistor 256 is turned on (driving pulse φHCLR: high) to reset again the horizontal transfer line 258. By repeating a series of these operations a predetermined times (two times in FIG. 6, more preferably, several tens of times), line-black reference signals are added on to the front end of the phase adjusting signal line.

Then by turning on the phase adjusting signal generator 29 (driving pulse φVREF: high) and alternately impressing the multiplexer 26 with a low level and a high level of the driving pulse φMUXSEL a predetermined times (e.g., 10 to 100 times), the reference voltage Vref1 and the phase adjusting signal Vref2 are alternately output to the output unit 31. The phase adjusting signal line is thus output.

A black reference signal line is output next. The variable voltage VRdmy is set to a level of the reference signal voltage Vfd_H (e.g., 2 V) and the variable voltage VR is set to a level of VDD (e.g., 3.3 V). With the variable voltage VR kept at a level of VDD, the drive signal φRdmy is impressed on the gate of the reference signal generation reset unit 236a. In this manner, the gate of the reference signal generation source follower transistor 237a is impressed with the reference signal voltage Vfd_H, and the pixel source follower transistor 237 is set to the on-state. The reference signal generator 247 is thus selected (selecting operation).

At the same time, a column-black reference signal generated in the reference signal generator 247 is output from the reference signal generator 247 to the vertical transfer line 239. In this state, by switching the clamp switch 253 from the on-state (φVCL: high) to the off-state (φVCL: low), the gate of the column source follower transistor 244 is set to the clamp voltage Vclp. The clamp voltage Vclp is determined by the timing of falling of the φVSH, and the reference signal voltage Vfd_H and the reference voltage Vref1 are also determined at this timing. The signal output to the gate of the column source follower transistor 244 is a sampled signal taking the clamp voltage Vclp as a reference.

After sampling the column-black reference signal taking the clamp voltage Vclp as a reference, the horizontal reset transistor 256 is turned off (φHCLR: low) to cancel the reset-state of the horizontal transfer line 258, the column selecting switch 254 provided in the most-downstream of the vertical transfer line 239a is turned on (driving pulse φHdmy: high), and the sample and hold switch 262 is turned on (driving pulse φHSH: high) in a pulsed manner, and thereby a line-black reference signal is transferred to the horizontal transfer line 258 to be sampled by the sample capacitor 263. The multiplexer 26 is impressed with driving pulse φMUXSEL of low level to output the line-black reference signal sampled by the sample capacitor 263 to the output unit 31. In this state, synchronizing with a driving pulse for the multiplexer 26, the horizontal reset transistor 256 is turned on (driving pulse.φHCLR: high) to reset again the horizontal transfer line 258. By repeating a series of these operations a predetermined times (two times in FIG. 6, more preferably, several tens of times), line-black reference signals are added on to the front end of the phase adjusting signal line.

Then the horizontal reset transistor 256 is turned off (φHCLR: low) to cancel the reset-state of the horizontal transfer line 258, the column selecting switch 254 of column <0> is turned on (driving pulse φHCLK<0>: high), and the sample and hold switch 262 is turned on (driving pulse φHSH: high) in a pulsed manner, and thereby a column-black reference signal in the column <0> is transferred to the horizontal transfer line 258 to be sampled by the sample capacitor 263. The multiplexer 26 is impressed with driving pulse φMUXSEL of low level to output the line-black reference signal sampled by the sample capacitor 263 to the output unit 31. In this state, synchronizing with a driving pulse for the multiplexer 26, the horizontal reset transistor 256 is turned on (driving pulse φHCLR: high) to reset again the horizontal transfer line 258.

Then the horizontal reset transistor 256 is turned off (φHCLR: low) to cancel the reset-state of the horizontal transfer line 258, the column selecting switch 254 of column <1> is turned on (driving pulse φHCLK<1>: high), and the sample and hold switch 262 is turned on (driving pulse φHSH: high) in a pulsed manner, and thereby a column-black reference signal in column <1> is transferred to the horizontal transfer line 258 to be sampled by the sample capacitor 263. The multiplexer 26 is impressed with driving pulse φMUXSEL of low level to output the line-black reference signal sampled by the sample capacitor 263 to the output unit 31. In this state, synchronizing with a driving pulse for the multiplexer 26, the horizontal reset transistor 256 is turned on (driving pulse φHCLR: high) to reset again the horizontal transfer line 258.

When line-black reference signals in all pixel columns have been output, by turning on the phase adjusting signal generator 29 (driving pulse φVREF: high) and alternately impressing the multiplexer 26 with a low level and a high level of the driving pulse φMUXSEL a predetermined times (e.g., several tens of times), the reference voltage Vref1 and the phase adjusting signal Vref2 are alternately output to the output unit 31. The black reference signal line is thus output.

Then the variable voltage VRdmy and the variable voltage VR are set to a level of Vfd_L (e.g., 1 V). With the variable voltage VRdmy and the variable voltage VR kept at a level of Vfd_L, the drive signal φRdmy is impressed on the gate of the reference signal generation reset unit 236a in a pulsed manner. In this manner, the gate of the reference signal generation source follower transistor 237a is impressed with the deselecting voltage Vfd_L, and the reference signal generation source follower transistor 237a is set to the off-state. The reference signal generator 247 is deselected in this manner (deselecting operation).

The operation of outputting a black reference signal line is repeated a predetermined times (two or more times, more preferably, 10 to 100 times) to output black reference signals in a plurality of lines. Black reference signals in a plurality of lines are later averaged and used for imaging signal processing. When the output of black reference signals is finished, the line counter is reset and readout of imaging signals starts from pixel line <0>.

The imaging signal line of line <0> (imaging signal line <0>) is output next. The variable voltage VR is set to a level of VDD (e.g., 3.3 V). With the variable voltage VR kept at a level of VDD, drive signal φR<0> is impressed on the gate of the pixel resetting unit 236 of pixel line <0> in a pulsed manner. Thus the gate of the pixel source follower transistor 237 of the pixel line <0> is impressed with the power source voltage VDD, and the pixel source follower transistor 237 is set to the on-state. The unit pixel 230 included in the pixel line <0> is selected in this manner (selecting operation).

At the same time, the variation unique to the unit pixel 230 to be readout and the noise signal including noise during reset of the pixel are output from the unit pixel 230 to the vertical transfer line 239. In this state, by switching the clamp switch 253 from the on-state (φVCL: high) to the off-state (φVCL: low), the gate of the column source follower transistor 244 is set to the clamp voltage Vclp. The clamp voltage Vclp is determined at a timing of falling of φVSH.

By turning on the transfer transistor 234 (driving pulse φT<0>: high) in a pulsed manner with the clamp switch 253 turned off (φVCL: low), the signal resulting from conversion in the charge converter 233 performed to a charge resulting from photoelectric conversion performed in the photoelectric conversion element 231 is read out into the vertical transfer line 239. In this operation, imaging signals from which noise signals are removed (optical signal) are output to the gate of the column source follower transistor 244 via the transfer capacitor 252. The signal output to the gate of the column source follower transistor 244 is a sampled signal taking the clamp voltage Vclp as a reference.

After sampling the imaging signal taking the clamp voltage Vclp as a reference, the horizontal reset transistor 256 is turned off (φHCLR: low) to cancel the reset-state of the horizontal transfer line 258, the column selecting switch 254 provided in the most-downstream of the vertical transfer line 239a is turned on (driving pulse φHdmy: high), and the sample and hold switch 262 is turned on (driving pulse φHSH: high) in a pulsed manner, and thereby a line-black reference signal is transferred to the horizontal transfer line 258 to be sampled by the sample capacitor 263. The multiplexer 26 is impressed with the driving pulse φMUXSEL of low level to output the line-black reference signal sampled by the sample capacitor 263 to the output unit 31. In this state, synchronizing with a driving pulse for the multiplexer 26, the horizontal reset transistor 256 is turned on (driving pulse φHCLR: high) to reset again the horizontal transfer line 258. By repeating a series of these operations a predetermined times (two times in FIG. 6, more preferably, several tens of times), line-black reference signals are added on to the front end of the imaging signal line <0>.

Then the horizontal reset transistor 256 is turned off (φHCLR: low) to cancel the reset-state of the horizontal transfer line 258, the column selecting switch 254 of the column <0> is turned on (driving pulse φHCLK<O>: high), and the sample and hold switch 262 is turned on (driving pulse φHSH: high) in a pulsed manner, and thereby an imaging signal in the column <0> is transferred to the horizontal transfer line 258 to be sampled by the sample capacitor 263. The multiplexer 26 is impressed with the driving pulse φMUXSEL of low level to output the imaging signal sampled by the sample capacitor 263 to the output unit 31. In this state, synchronizing with a driving pulse for the multiplexer 26, the horizontal reset transistor 256 is turned on (driving pulse φHCLR: high) to reset again the horizontal transfer line 258.

Then the horizontal reset transistor 256 is turned off (φHCLR: low) to cancel the reset-state of the horizontal transfer line 258, the column selecting switch 254 of column <1> is turned on (driving pulse φHCLK<1>: high), and the sample and hold switch 262 is turned on (driving pulse φHSH: high) in a pulsed manner, and thereby an imaging signal in the column <1> is transferred to the horizontal transfer line 258 to be sampled by the sample capacitor 263. The multiplexer 26 is impressed with the driving pulse φMUXSEL of low level to output the imaging signal sampled by the sample capacitor 263 to the output unit 31. In this state, synchronizing with a driving pulse for the multiplexer 26, the horizontal reset transistor 256 is turned on (driving pulse φHCLR: high) to reset again the horizontal transfer line 258.

When imaging signals of the all pixel columns have been output, by turning on the phase adjusting signal generator 29 (driving pulse VREF: high) and alternately impressing the multiplexer 26 with a low level and a high level of the driving pulse φMUXSEL a predetermined times (e.g., several tens of times), the reference voltage Vref1 and the phase adjusting signal Vref2 are alternately output to the output unit 31. The imaging signal line <0> is thus output.

When imaging signals for one line are output, the variable voltage VR is set to a level of Vfd_L (e.g., 1 V). With the variable voltage VR kept at a level of Vfd_L, the drive signal 4R<0> is impressed on the gate of the pixel resetting unit 236 of the selected pixel line <0> in a pulsed manner. Thus the gate of the pixel source follower transistor 237 of the pixel line <0> is impressed with the deselecting voltage Vfd_L, and the pixel source follower transistor 237 is set to the off-state. The unit pixel 230 included in the pixel line <0> is deselected in this manner (deselecting operation).

By repeating the readout operation for one line for the number of unit pixel lines (or the number of lines to be read out), imaging signals for one frame are output.

Figure 7:
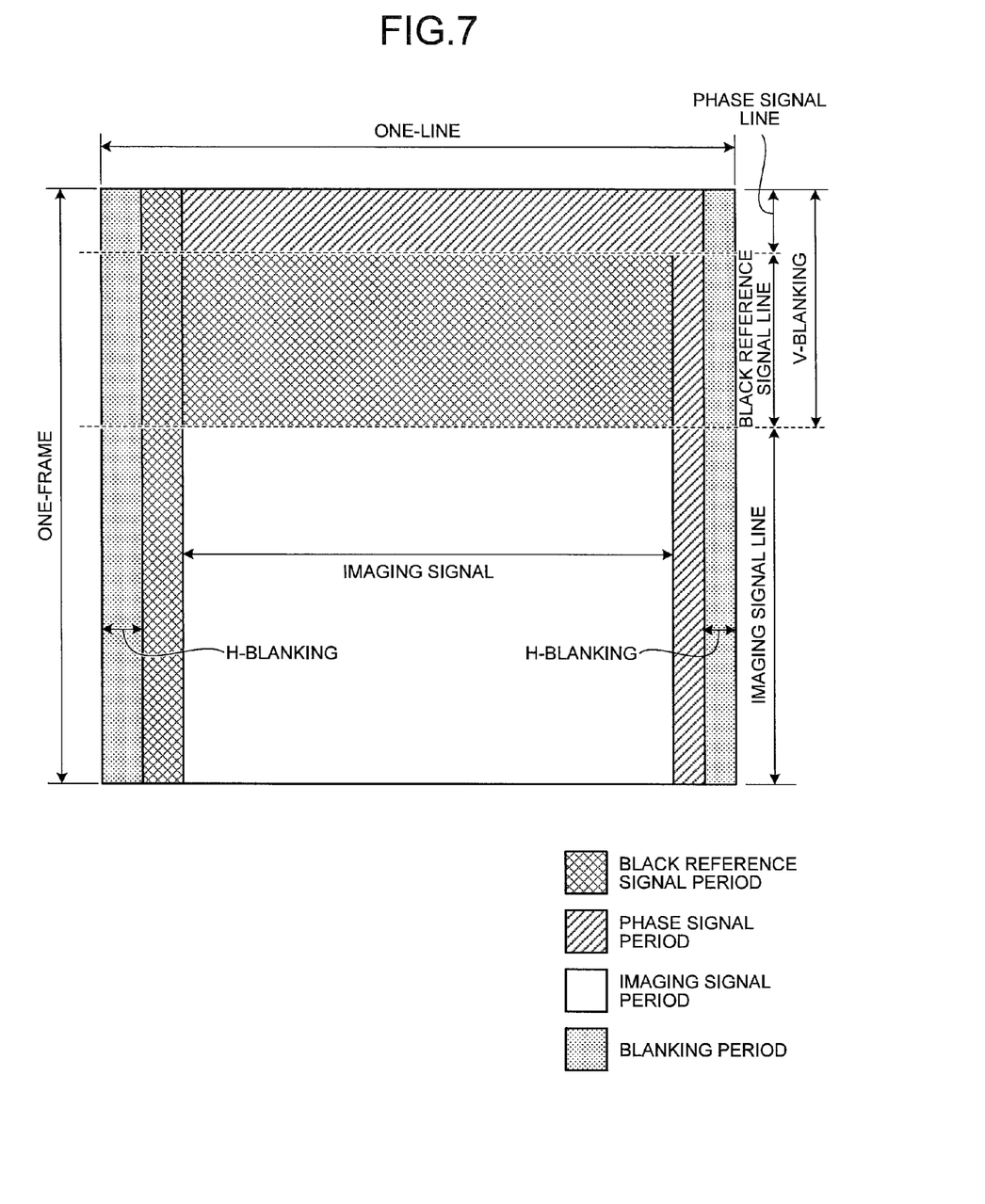
FIG. 7 is a schematic drawing illustrating a signal output format according to the embodiment of the present invention.

FIG. 7 is a schematic drawing illustrating a signal output format according to the embodiment of the present invention. In a conventional imaging device, no signal is transmitted from an imaging element to, for example, a signal processing device during a blanking period, as well as a vertical blanking period (V-blanking) and a horizontal blanking period (H-blanking). So that fluctuation in power source voltage caused by the change in power consumption between an imaging signal period and a blanking period may occur, which results in distortion of image signals that is, distortion of an image.

As illustrated in FIG. 7, the imaging unit 20 according to the embodiment of the present invention transmits a phase adjusting signal generated in the phase adjusting signal generator 29 and a column-black reference signal generated in the reference signal generator 247 to the connecting unit 5 during the vertical blanking period (V-blanking). Thus an amount of power almost equivalent to that in the imaging signal period is consumed during the blanking period. Consequently, fluctuation in power source voltage caused by fluctuation in power consumption can be suppressed.

Moreover, after the horizontal blanking period (H-blanking), a line-black reference signal generated in the reference signal generator 248 is transmitted to the connecting unit 5 before the start of transmission of imaging signals in each line. Thus, fluctuation in power source voltage caused by fluctuation in power consumption during transition from the blanking period to the imaging signal period can be suppressed.

Moreover, after finishing transmission of imaging signals in each line, a phase adjusting signal generated in the phase adjusting signal generator 29 is transmitted to the connecting unit 5 before the horizontal blanking period (H-blanking).

According to the embodiment of the present invention, fluctuation in power consumption of the whole imaging element 20 can be suppressed because a phase adjusting signal is transmitted to the connecting unit 5 during the blanking period. Deterioration in the quality of image caused by fluctuation in power source can be suppressed.

With a phase adjusting signal transmitted to the connecting unit 5, the drive timing of the AFE unit 51 can be adjusted. Even when a delay occurs by using the long transmission cable 3 such as in the endoscope 2, the drive timings of the imaging unit 20 and the AFE unit 51 can be synchronized. The quality of image can thus be improved.

Furthermore, the reference signal generator 247 not including the photoelectric conversion element (photodiode) 231 is provided to each column of the unit pixel 230 at the same pitch as the unit pixels 230, so that the black reference signal in each column of the unit pixel 230 can be output. Use of black reference signals in the imaging signal processing unit 52 enables, for example, removal of vertical lines or reduction of black noise. Thus a high quality image can be obtained.

Furthermore, the reference signal generator 248 not including the photoelectric conversion element (photodiode) 231 is provided apart from the column of the unit pixel 230, and a black reference signal is read out a predetermined times (two or more times, more preferably, several tens of times) from the reference signal generator 248 before readout of signals from the lines of the unit pixel 230, so that black reference signals corresponding to a plurality of columns are located in the front end of a series of signals in each line. Use of black reference signals in the imaging signal processing unit 52 enables, for example, reduction of side lines. Thus a high quality image can be obtained.

Furthermore, since the reference signal generators 247 and 248 do not include the photoelectric conversion element 231, a light blocking drape or the like for outputting black reference signals needs not be provided. Basically, the reference signal generator 247 having no light reacting properties needs not be provided to a plurality of lines to eliminate the effect from leaked light. So that the downsizing of the imaging element as well as the high quality of an image can be achieved.

The imaging element 20 according to the embodiment transfers the black reference signal generated in the reference signal generator 247 to the connecting unit 5 during transition from the horizontal blanking period to the imaging signal period, so that fluctuation in power source voltage caused by fluctuation in power consumption can be suppressed. Deterioration in the quality of image caused by fluctuation in power source can be suppressed.

Since the noise remover 243 does not require a capacitor for sampling (sampling capacitor), the capacity of the transfer capacitor (AC coupling capacitor) 252 can be reduced to be small. Without a sampling capacitor, the area occupied by the noise remover 243 can be reduced.

Moreover, an imaging signal and the reference voltage Vref can alternately be output for each pixel. In this manner, common mode noise superimposed on a transmitted signal in, for example, a correlated double sampling circuit provided in the connecting unit 5 can effectively be removed.

Either or both of the reference signal generators 247 and 248 can be omitted. The sample and hold unit 255 can also be omitted. Even when the sample and hold unit 255 is omitted, only imaging signals are selected by the multiplexer 26 in the downstream and an imaging signal and the reference voltage Vref are alternately output to the output unit 31.

In the embodiment, a unit cell is composed of a single photoelectric conversion element without sharing a pixel. Although, a unit cell may be composed of a set of a plurality of photoelectric conversion elements. In this case, for example, a unit cell may be composed of a set of two photoelectric conversion elements adjacent in a column-direction, a set of two photoelectric conversion elements adjacent in a line-direction, and a set of four photoelectric conversion elements in which two pairs of photoelectric conversion elements are adjacent in a line-direction, where two photoelectric conversion elements in each pair are adjacent in a column-direction.

Furthermore, in the embodiment, each of the unit pixel 230 and the reference signal generators 247 and 248 does not include a pixel-output switch transistor. Although, each of the unit pixel 230 and the reference signal generators 247 and 248 may include a pixel-output switch transistor. In this case, the unit pixel 230 and the reference signal generator 247 are selected or deselected by a drive signal input to the gate of the pixel-output switch transistor.

It is possible to provide the imaging element, the imaging device, the endoscope, and the endoscope system, and the method of driving the imaging element that stabilize a power source voltage and can suppress degradation in image quality.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging element comprising:
    a plurality of pixels disposed in an arrangement of a two-dimensional matrix, the pixels being configured to receive external light to generate an imaging signal corresponding to a light amount and output the imaging signal;
    first vertical transfer lines, each first vertical transfer line being provided to each column in the arrangement of the plurality of pixels and transferring the imaging signal;
    a second vertical transfer line provided discretely from the first vertical transfer line;
    a reference voltage generator configured to generate a first reference voltage for a column-black reference signal, a second reference voltage for a line-black reference signal and a third reference voltage for phase adjustment;
    a phase adjusting signal generator configured to output a phase adjusting signal corresponding to the third reference voltage during a period in which the pixel does not output the imaging signal, the phase adjusting signal being used for the phase adjustment;
    a first reference signal generator including a first source follower transistor connected to the first vertical transfer line and a first reset transistor supplying an output voltage of the reference voltage generator to a gate of the first source follower transistor, and the first reference signal generator being configured to generate a column-black reference signal corresponding to the first reference voltage and output the column-black reference signal to the first vertical transfer line;
    a second reference signal generator including a second source follower transistor connected to the second vertical transfer line and a second reset transistor supplying the second reference voltage to a gate of the second source follower transistor, and the second reference signal generator being configured to generate a line-black reference signal corresponding to the second reference voltage and output the line-black reference signal to the second vertical transfer line; and
    a timing generator configured to drive the phase adjusting signal generator, the first reference signal generator and the second reference signal generator to transmit the phase adjusting signal, the column-black reference signal and the line-black reference signal, respectively, to an external device during a transfer blanking period of the imaging signal.

2. The imaging element according to claim 1, wherein the timing generator is configured to further transmit the line-black reference signal to the external device before starting transmission of the imaging signal of each column in the arrangement of the plurality of pixels to the external device after a horizontal blanking period of the imaging signal.

3. The imaging element according to claim 1, wherein the timing generator is configured to further transmit the phase adjusting signal to the external device before a horizontal blanking period of the imaging signal after completing transmission of the imaging signal of each column in the arrangement of the plurality of pixels to the external device.

4. An imaging device comprising
    an imaging element comprising:
        a plurality of pixels disposed in an arrangement of a two-dimensional matrix, the pixels being configured to receive external light to generate an imaging signal corresponding to a light amount and output the imaging signal;
        first vertical transfer lines, each first vertical transfer line being provided to each column in the arrangement of the plurality of pixels and transferring the imaging signal;
        a second vertical transfer line provided discretely from the first vertical transfer line;
        a reference voltage generator configured to generate a first reference voltage for a column-black reference signal, a second reference voltage for a line-black reference signal and a third reference voltage for phase adjustment;
        a phase adjusting signal generator configured to output a phase adjusting signal corresponding to the third reference voltage during a period in which the pixel does not output the imaging signal, the phase adjusting signal being used for the phase adjustment;
        a first reference signal generator including a first source follower transistor connected to the first vertical transfer line and a first reset transistor supplying an output voltage of the reference voltage generator to a gate of the first source follower transistor, and the first reference signal generator being configured to generate a column-black reference signal corresponding to the first reference voltage and output the column-black reference signal to the first vertical transfer line;
        a second reference signal generator including a second source follower transistor connected to the second vertical transfer line and a second reset transistor supplying the second reference voltage to a gate of the second source follower transistor, and the second reference signal generator being configured to generate a line-black reference signal corresponding to the second reference voltage and output the line-black reference signal to the second vertical transfer line; and a timing generator configured to drive the phase adjusting signal generator, the first reference signal generator and the second reference signal generator to transmit the phase adjusting signal, the column-black reference signal and the line-black reference signal, respectively, to an external device during a transfer blanking period of the imaging signal.

5. An endoscope comprising an imaging device on a distal end side of an insertion part, wherein
the imaging device comprising an imaging element comprising:

a plurality of pixels disposed in an arrangement of a two-dimensional matrix, the pixels being configured to receive external light to generate an imaging signal corresponding to a light amount and output the imaging signal;

first vertical transfer lines, each first vertical transfer line being provided to each column in the arrangement of the plurality of pixels and transferring the imaging signal;

a second vertical transfer line provided discretely from the first vertical transfer line;

a reference voltage generator configured to generate a first reference voltage for a column-black reference signal, a second reference voltage for a line-black reference signal and a third reference voltage for phase adjustment;

a phase adjusting signal generator configured to output a phase adjusting signal corresponding to the third reference voltage during a period in which the pixel does not output the imaging signal, the phase adjusting signal being used for the phase adjustment;

a first reference signal generator including a first source follower transistor connected to the first vertical transfer line and a first reset transistor supplying an output voltage of the reference voltage generator to a gate of the first source follower transistor, and the first reference signal generator being configured to generate a column-black reference signal corresponding to the first reference voltage and output the column-black reference signal to the first vertical transfer line;

a second reference signal generator including a second source follower transistor connected to the second vertical transfer line and a second reset transistor supplying the second reference voltage to a gate of the second source follower transistor, and the second reference signal generator being configured to generate a line-black reference signal corresponding to the second reference voltage and output the line-black reference signal to the second vertical transfer line; and a timing generator configured to drive the phase adjusting signal generator, the first reference signal generator and the second reference signal generator to transmit the phase adjusting signal, the column-black reference signal and the line-black reference signal, respectively, to an external device during a transfer blanking period of the imaging signal.

6. An endoscope system comprising:
an endoscope comprising an imaging device on a distal end side of an insertion part; and
a processing unit configured to convert the imaging signal into an image signal, wherein
the imaging device comprising an imaging element comprising:

a plurality of pixels disposed in an arrangement of a two-dimensional matrix, the pixels being configured to receive external light to generate an imaging signal corresponding to a light amount and output the imaging signal;

first vertical transfer lines, each first vertical transfer line being provided to each column in the arrangement of the plurality of pixels and transferring the imaging signal;

a second vertical transfer line provided discretely from the first vertical transfer line;

a reference voltage generator configured to generate a first reference voltage for a column-black reference signal, a second reference voltage for a line-black reference signal and a third reference voltage for phase adjustment;

a phase adjusting signal generator configured to output a phase adjusting signal corresponding to the third reference voltage during a period in which the pixel does not output the imaging signal, the phase adjusting signal being used for the phase adjustment;

a first reference signal generator including a first source follower transistor connected to the first vertical transfer line and a first reset transistor supplying an output voltage of the reference voltage generator to a gate of the first source follower transistor, and the first reference signal generator being configured to generate a column-black reference signal corresponding to the first reference voltage and output the column-black reference signal to the first vertical transfer line;

a second reference signal generator including a second source follower transistor connected to the second vertical transfer line and a second reset transistor supplying the second reference voltage to a gate of the second source follower transistor, and the second reference signal generator being configured to generate a line-black reference signal corresponding to the second reference voltage and output the line-black reference signal to the second vertical transfer line; and a timing generator configured to drive the phase adjusting signal generator, the first reference signal generator and the second reference signal generator to transmit the phase adjusting signal, the column-black reference signal and the line-black reference signal, respectively, to an external device during a transfer blanking period of the imaging signal.

* * * * *